United States Patent
Qiu et al.

(10) Patent No.: US 10,393,846 B2
(45) Date of Patent: Aug. 27, 2019

(54) FUNCTIONAL MAGNETIC RESONANCE IMAGING QUALITY DETECTION PHANTOM AND METHOD

(71) Applicant: TAISHAN MEDICAL UNIVERSITY, Tai'an, Shandong (CN)

(72) Inventors: Jianfeng Qiu, Tai'an (CN); Guozhu Wang, Tai'an (CN)

(73) Assignee: TAISHAN MEDICAL UNIVERSITY, Tai'an (CN)

(*) Notice: Subject to any disclaimer, the term of this patent is extended or adjusted under 35 U.S.C. 154(b) by 149 days.

(21) Appl. No.: 15/572,443

(22) PCT Filed: Mar. 13, 2017

(86) PCT No.: PCT/CN2017/076479
§ 371 (c)(1),
(2) Date: Nov. 7, 2017

(87) PCT Pub. No.: WO2018/054024
PCT Pub. Date: Mar. 29, 2018

(65) Prior Publication Data
US 2018/0284213 A1    Oct. 4, 2018

(30) Foreign Application Priority Data
Sep. 23, 2016  (CN) .......................... 2016 1 0847595

(51) Int. Cl.
*G01V 3/00* (2006.01)
*G01R 33/58* (2006.01)
(Continued)

(52) U.S. Cl.
CPC ............ *G01R 33/58* (2013.01); *A61B 5/0042* (2013.01); *A61B 5/055* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS

2014/0225612 A1* 8/2014 Polimeni ............ G01R 33/4835
324/309
2015/0309149 A1* 10/2015 Holdsworth ........... G01R 33/58
324/309

FOREIGN PATENT DOCUMENTS

CN      201259533 Y      6/2009
CN      201259534 Y      6/2009
(Continued)

OTHER PUBLICATIONS

Jun. 28, 2017 International Search Report issued in International Application No. PCT/CN2017/076479.

*Primary Examiner* — Walter L Lindsay, Jr.
*Assistant Examiner* — Frederick Wenderoth
(74) *Attorney, Agent, or Firm* — Oliff PLC

(57) ABSTRACT

Disclosed is a functional magnetic resonance imaging quality detection phantom and method. The phantom includes two independent shells which are movably connected with each other, wherein a BOLD simulation signal module is arranged in the first shell, and a basic imaging detection module is arranged in the second shell; the BOLD simulation signal module includes a locating accuracy test component and a BOLD signal simulation component, the locating accuracy test component includes two locating blocks placed in a crossing manner, a wedge-shaped passage composed of isosceles right triangle blocks is arranged on the locating blocks, and the BOLD signal simulation component includes an artificial brain for functional magnetic resonance imaging; and the present invention can simulate human body BOLD signal changes and simulate a brain (Continued)

activation area in a magnetic resonance system, and is for the test analysis and researches on the accuracy, reliability and repeatability of brain function imaging.

14 Claims, 2 Drawing Sheets

(51) Int. Cl.
  *A61B 5/00* (2006.01)
  *A61B 5/055* (2006.01)
  *G01R 33/48* (2006.01)
  *G01R 33/56* (2006.01)
  *A61B 5/145* (2006.01)

(52) U.S. Cl.
  CPC ..... *G01R 33/4806* (2013.01); *G01R 33/5607* (2013.01); *A61B 5/14542* (2013.01); *A61B 5/7235* (2013.01); *A61B 2560/0228* (2013.01); *A61B 2576/026* (2013.01)

(58) Field of Classification Search
  USPC .......................................................... 324/309
  See application file for complete search history.

(56) References Cited

FOREIGN PATENT DOCUMENTS

| | | |
|---|---|---|
| CN | 203591259 U | 5/2014 |
| CN | 106377261 A | 2/2017 |
| WO | 2009/004297 A2 | 1/2009 |

\* cited by examiner

FUNCTIONAL MAGNETIC RESONANCE IMAGING QUALITY DETECTION PHANTOM AND METHOD

FIELD OF THE INVENTION

The present invention relates to a functional magnetic resonance imaging quality detection phantom and method, in particular relates to an imaging quality detection phantom of magnetic resonance for brain function imaging (task state) based on BOLD (blood oxygenation level dependent) signals, and specifically relates to an imaging model simulating human body BOLD signal changes and simulating brain activation area in a magnetic resonance system for the test analysis and researches on the accuracy, reliability and repeatability of brain function imaging.

BACKGROUND OF THE INVENTION

Magnetic resonance brain function imaging is based on the BOLD phenomenon. T2* signal (actual $T_2$ relaxation time) difference (task state functional magnetic resonance) between the task state brain section image and the static state brain section image is generally detected through fast imaging sequence scanning, and a corresponding stimulated brain function area is determined through image processing and statistic analysis. Because the BOLD signal exits for an extremely short time (3-6 ms), the brain function area cannot be verified by the anatomical gold standard. Therefore, the accuracy and the repeatability of brain function imaging have been low all the time, and also the brain function analysis results have been controversial all the time. In this case, a simulative BOLD signal is required, and imaging result calibration and verification of the analysis results of the brain function area and the brain connection are carried out in coordination with a test standard of brain function magnetic resonance imaging (imaging and data analysis).

SUMMARY OF THE INVENTION

In order to solve the above problem, the present invention provides a functional magnetic resonance imaging quality detection phantom and method, and the present invention has the following characteristics: (1) it has a brain appearance, and the morphological simulation degree of magnetic resonance imaging is high; (2) the uniformity of a magnetic field is disturbed by an external current to form a BOLD simulation module with regional $T_2$* signal changes (enhancement); (3) it has resolution, geometric distortion signal to noise ratio and other basic magnetic resonance imaging detection modules, which has detection versatility; and (4) the phantom is provided with an external programmable power supply controller, which can remotely control the on-off of the current, the duration and the pulse frequency of the BOLD simulation module outdoors. The control solution can be combined with the fast sequence of functional magnetic resonance imaging to set a stimulation solution.

In order to achieve the above objective, the present invention adopts the following technical solution:

A functional magnetic resonance imaging quality detection phantom includes two independent shells which are movably connected with each other, wherein a BOLD simulation signal module is arranged in the first shell, and a basic imaging detection module is arranged in the second shell;

the BOLD simulation signal module includes a locating accuracy test component and a BOLD signal simulation component, wherein the locating accuracy test component includes two locating blocks placed in a crossing manner, a wedge-shaped passage composed of isosceles right triangle blocks is arranged on the locating blocks, and the BOLD signal simulation component includes an artificial brain for functional magnetic resonance imaging; and the basic imaging detection module includes a locating accuracy test component, a geometric distortion test component, a high contrast component and a layer deviation measurement component, which are independent from each other, wherein the geometric distortion test component is of a multilayer grid structure to simulate the geometric distortion degrees of images in each direction; the high contrast component includes a substrate and multiple rows of through holes with different apertures formed in the substrate; and the layer deviation measurement component includes a basement layer and two orthogonal gaps formed on the basement layer.

Preferably, both the first shell and the second shell are cylindrical shells made of organic glass, the two shells have the same diameter, and the height of the first shell is larger than that of the second shell.

Preferably, bayonets are formed in outer sides of both the first shell and the second shell, and the two shells are connected together through the bayonets.

Preferably, the first shell and the second shell are filled with magnetic resonance standard test solution, for example, copper sulfate, distilled water, sodium chloride or nickel chloride.

Preferably, the geometric distortion test component includes multiple layers of grids, the aperture of the check of each grid is the same, and the thicknesses of the sides of the checks are the same, the distance between the vertexes of two arbitrary checks is measured on the obtained image by scanning each layer, the distance is compared with the real distance to obtain the geometric distortion degree of the image on the axial direction, and the distances between the vertexes of the checks of different layers are measured to obtain the geometric distortion on a sagittal direction and a coronal direction.

Preferably, the grids are made of a PVC material, and three layers of grids are arranged.

Preferably, multiple rows of through holes with different diameters are formed in the substrate of the high contrast component, multiple through holes are formed in each row, the diameters of the through holes on the same row are the same size, the intervals between the neighboring through holes having the same diameters are equal to their diameters, through hole images are observed on the obtained image by scanning, and if the holes having the same diameters are clear and the signals are not connected with each other, the minimum aperture satisfying the condition is a limit visual width.

Preferably, the wedge shapes on the locating blocks of the locating accuracy test component are arranged in a crossing manner, a locating line is arranged at the intersection of long sides of the two locating blocks, if the lengths of black long dark strips formed in the scanned image are equal, it indicates that the locating is accurate, otherwise, there is a locating deviation.

Preferably, gaps with a 45-degree angle are formed on the basement layer of the layer deviation measurement component, the two gaps are orthogonal, the widths of the gaps are the same, and an actual layer thickness is calculated and confirmed through a signal formed by the two gaps on the scanned image to obtain a setting layer thickness deviation.

Preferably, a setting area in the second shell is scanned to obtain the signal, noise and variance value of the area, and the signal to noise ratio of the image is calculated.

Preferably, the artificial brain in the shape of the BOLD signal simulation component is made of hydrogel containing 0.5-1% of copper sulfate, 0.3-0.5% of sodium chloride, 1-1.25% of agarose, 0.100-0.125% of Gd-DTPA (gadolinium diethylene triamine pentaacetic acid) and is used for simulating $T_1$ and $T_2$ relaxation values of a gray matter of a human brain under magnetic resonance.

Preferably, the artificial brain has the structure shape of a human brain, an opisthencephalon, a ventricle and a gyrus. The morphological data of the artificial brain are from the ICBM (International Consortium for Brain Mapping) of the Montreal Neurological Institute, and it is a standard brain three-dimensional matrix integrating 152 actual brains, the contour of the digital brain is obtained by 3D printing, and then a material is filled to form an artificial brain entity.

Preferably, a hollow cavity is respectively arranged on a frontal lobe position and a sea horse position of the artificial brain corresponding to the transverse short axis direction of the first shell, is away from the surface gyrus for 1 cm and 5 cm respectively, and is used for simulating the BOLD signals of the frontal lobe area and the sea horse area (the sea horse and amygdaloid nucleus have lower bold signals) and simulating cognitive function areas of the human brain. A hollow cavity is respectively arranged at a gyrus cinguli position of the artificial brain corresponding to the longitudinal long axial line direction of the first shell, is away from the surface gyrus for 3 cm and is used for simulating the BOLD signals of the gyrus cinguli of the human brain.

Preferably, a coil extends out from the first shell along the longitudinal axial line direction of the first shell and is connected with an external power supply controller through a connecting line.

Preferably, the external power supply controller is a programmable controller, and controls the turn-on, duration or turn-off between power supply and the coils and meanwhile controls the on/off time, duration and frequency.

A detection method based on the above detection phantom includes the following steps:

during conventional scanning of the artificial brain component, the three coils are in a turned off state, and the water molecules in the hollow cavities and the water molecules in the gel are all in a normal magnetic resonance signal imaging state;

during task state scanning, turning on and turning off the external power supply controller according to set pulse frequency in cooperation with a scanning sequence so as to generate pulse current through the coils in the corresponding hollow cavities, and changing the uniformity of a local magnetic field at the water molecules in the hollow cavities to cause a change in time; and realizing alternate and continuous occurrence of signal difference of conventional scanning and task state scanning to realize the BOLD signals of the artificial brain, and performing brain outline extraction on an obtained brain function magnetic resonance sequence image.

The present invention has the following beneficial effects:

(1) the present invention provides an imaging model for simulating human body BOLD signal changes and simulating the brain activation area in the magnetic resonance system for the test analysis and researches on the accuracy, reliability and repeatability of brain function imaging;

(2) the present invention can cooperate with the test standard of brain function magnetic resonance imaging (imaging and data analysis) to perform imaging result calibration and verification of the analysis results of the brain function area and the brain connection;

(3) the present invention has a brain appearance, the morphological simulation degree of magnetic resonance imaging is high, the uniformity of the magnetic field is disturbed by an external current to form regional $T_2^*$ signal changes;

(4) the present invention has resolution, geometric distortion, signal to noise ratio and other basic magnetic resonance imaging detection modules, and has detection versatility; and (5) the present invention can remotely control the on-off of the current, the duration, the pulse frequency of the BOLD simulation module outdoors so as to effectively guarantee the body health and safety of a simulation experimenter.

BRIEF DESCRIPTION OF THE DRAWINGS

FIG. 4 (b) is a front view of the layer deviation measurement component of the present invention;

DETAILED DESCRIPTION OF THE EMBODIMENTS

The present invention will be further illustrated below in combination with the drawings and embodiments.

Figure 1:
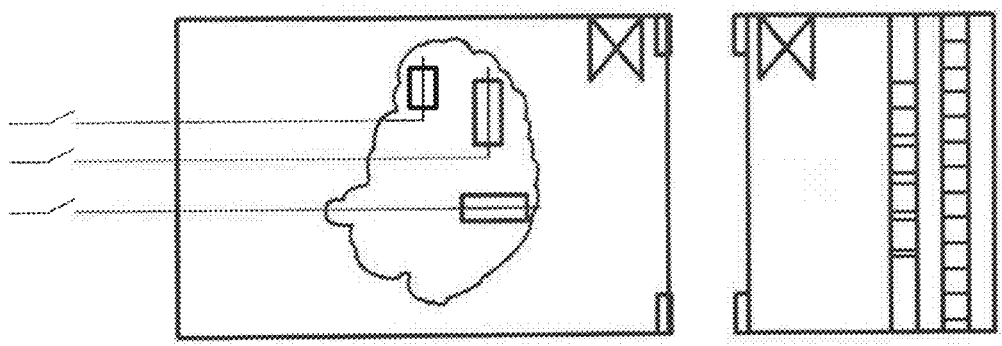
FIG. 1 is an external view of overall combination of a phantom of the present invention.

As shown in FIG. 1, a quality control and detection phantom suitable for medical functional magnetic resonance brain imaging and simulating BOLD signal changes includes a combinable and detachable overall structure (combinable and detachable outline module), a BOLD simulation signal module and a basic imaging detection module.

The combinable and detachable outline module includes a PMMA organic glass cylindrical shell with a diameter of 18 cm, and the shell is divided into two parts with the heights of 15 cm and 5 cm. The two parts are combinable and detachable, and their interiors do not communicate with each other. The cylinder with the height of 15 cm contains the BOLD simulation signal module, one end is sealed, and the other end is connected with an external power supply controller through a conducting wire. Two ends of the cylinder with the height of 5 cm are sealed, it can contain resolution, geometric distortion, signal to noise ratio and other basic imaging parameter detection modules, and the cylinders are filled with a magnetic resonance standard test solution (copper sulfate, distilled water, sodium chloride/ nickel chloride). The two cylinders can be combined through bayonets.

The BOLD simulation signal module and the basic imaging detection module contain square tenon structures made of a PMMA material on the two ends, and the connection and separation of the two modules of the phantom are realized by the linking and opening of the tenon structures. The two modules of the phantom can be combined for use (scanning) and can also be independently used.

Figure 2:
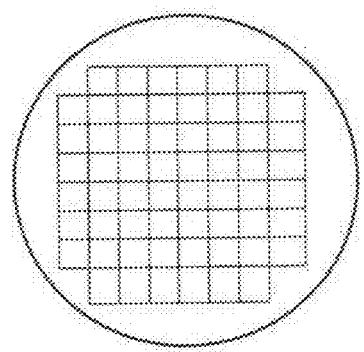
FIG. 2 is a schematic diagram of a geometric distortion test component of the present invention.

The basic imaging detection module contains 5 independent test components therein, which are respectively as follows:

(1) A geometric distortion test component consists of a rectangular square matrix, wherein the component is three layers of grids made of a PVC material. The aperture of each check of the grid is 3*3*3 mm$^3$, and the thickness of the PVC side of the check block is 1 mm. The distance between the vertexes of two arbitrary checks is measured on the obtained image by scanning the layer, and the distance is compared with the real distance to obtain the geometric distortion degree of the image on the axial direction. The grids are divided into three layers up and down, the PVC thickness among the layers is 1 mm, and the distances between the vertexes of the checks of different layers are measured to obtain the geometric distortion on a sagittal direction and a coronal direction, as shown in FIG. 2.

Figure 3:
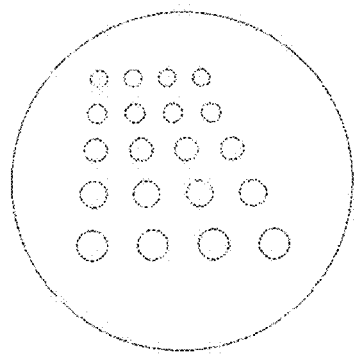
FIG. 3 is a schematic diagram of a high contrast test component of the present invention.

(2) A high contrast (limiting resolution) component is composed of through holes with different diameters, 5 rows of through holes with different diameters formed in a PMMA substrate, the apertures are 5 mm, 2.5 mm, 1 mm, 0.5 mm and 0.2 mm, and the intervals between the through holes having the same diameters are equal to their diameters, as shown in FIG. 3. Through hole images are observed on the obtained image by scanning the layer, and if the holes having the same diameters are clear and the signals are not connected with each other, the minimum aperture satisfying the condition is a limit visual width.

Figures 4A, 4B:
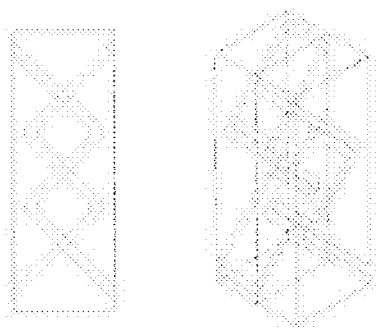
FIG. 4 (a) is a side view of a layer deviation measurement component of the present invention.

(3) A locating accuracy test component is composed of wedge-shaped isosceles right triangle blocks, wherein two isosceles right triangles are placed in a crossing manner, as shown in FIG. 4. When the layer is scanned, a locating line is arranged at the intersection of long sides of the two triangular blocks. If the locating is accurate, the lengths of black long dark strips formed by the triangular blocks in the image are equal. If the locating system has a deviation, the lengths of the two black long strips are not equal.

(4) A layer deviation measurement component is composed of strip-shaped PVC containing gaps, wherein the length of a PVC rectangular block is 6 mm, the width is 6 mm, the layer deviation measurement component includes two 45-degree gaps with the widths of 1 mm, and the two gaps are orthogonal. When the layer is scanned, two symmetrically distributed bright signals (caused by the test solution filled in the gaps) will occur on the image, the full widths at half maximum of the bright signals are measured, a product of the two full widths at half maximum is calculated, a square-root of the product is calculated to obtain an actual layer thickness, and the actual layer thickness is compared with a setting layer thickness to obtain a setting layer thickness deviation.

(5) An overflow layer component containing no physical object is used for measuring the signal to noise ratio, wherein when the layer is scanned, the obtained image can be used for selecting an interested area, and the signal to noise ratio of the image can be calculated by obtaining signal, noise and a variance value.

The BOLD simulation signal module includes a locating accuracy test component and a BOLD signal simulation component. The structure of the locating accuracy test component is basically consistent with that in the basic imaging detection module.

The outline of the BOLD signal simulation component is a 15*15*13 cm$^3$ artificial brain. The artificial brain is made of hydrogel containing 0.5-1% of copper sulfate, 0.3-0.5% of sodium chloride, 1-1.25% of agarose, 0.100-0.125% of Gd-DTPA (gadolinium diethylene triamine pentaacetic acid) and is used for simulating $T_1$ and $T_2$ relaxation values of a gray matter of a human brain under magnetic resonance.

The appearance of the artificial brain is obtained by the "Chinese digital" standard brain image simulation, and is registered with an ICBM standard brain. The artificial brain has the structure shape of a human brain, an opisthencephalon, a ventricle and a gyrus. The hydrogel has rich hydrogen protons, and can produce bright signals similar to the human brain brightness during the magnetic resonance scanning.

Figure 5:
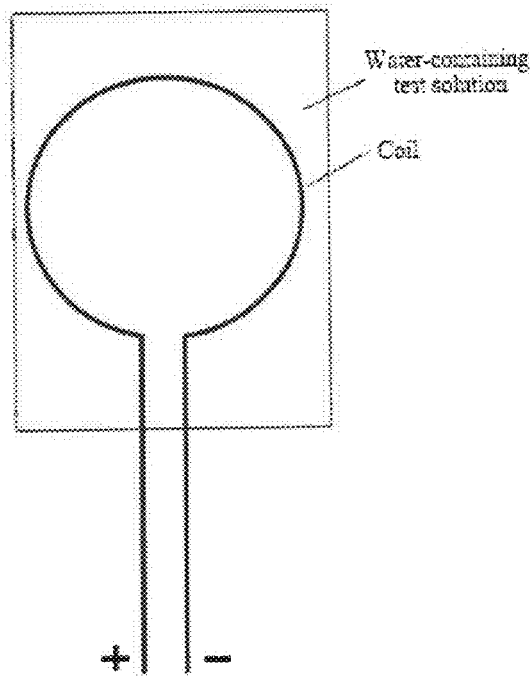
FIG. 5 is a schematic diagram of a shape of a coil in a rectangular space of an artificial brain of the present invention.

The artificial brain contains three small rectangular volume spaces therein, and the space is about 3375 mm$^3$ (about 125 27 mm$^3$ functional magnetic resonance imaging pixels and 3-4 scanning levels are occupied). The space contains a circular coil with a diameter of less than or equal to 2 mm therein, there is a single strand of coil, and the coil is coated by rubber and enters the space from the long axis direction of the phantom and penetrates through the space from the long axis direction after rounding for 350 degrees, as shown in FIG. 5. The coil is fixed in the space, and the space is filled with a magnetic resonance standard test solution (pure water, copper sulfate and sodium chloride).

The two rectangular volume spaces are located on the short axis direction of the phantom, are respectively located on a frontal lobe position and a sea horse position of the artificial brain, are away from the surface gyrus for 1 cm and 5 cm separately, and are used for simulating the BOLD signals of the frontal lobe area and the sea horse area (the sea horse and amygdaloid nucleus have lower bold signals) and simulating cognitive function areas of the human brain. A rectangular volume space is located on the long axis direction of the phantom, is located on a gyrus cinguli position of the artificial brain, is away from the surface gyrus for 3 cm and is used for simulating the BOLD signals of the gyrus cinguli of the human brain.

Figure 6:
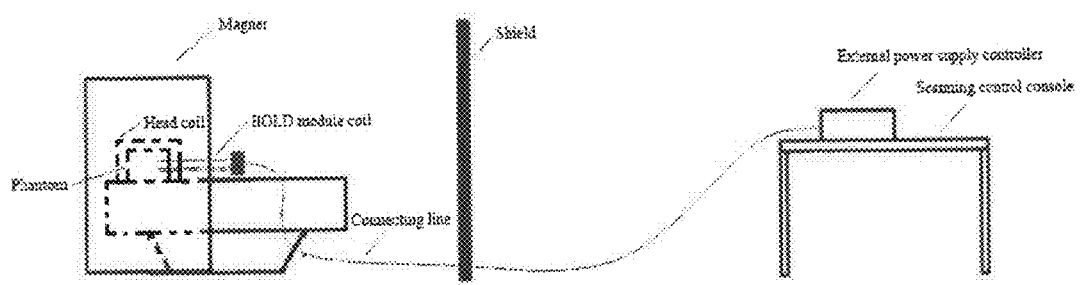
FIG. 6 is a schematic diagram of connection and use positions of the phantom of the present invention and an external power supply controller.

Two wiring ends of the coils in the three rectangular volume spaces penetrate through the phantom and are connected with the external power supply controller. The wiring length is not smaller than 5 m, so as to guarantee that the external power supply controller can be placed on an external operation room control console through a waveguide plate when the phantom is in a scanning state, as shown in FIG. 6.

The external power supply controller is a programmable controller, and the turn-on, duration or turn-off of the power supply is set by programming; and the on/off time, duration, frequency and times are set.

The BOLD simulation module can be used for functional magnetic resonance imaging. During conventional scanning of the artificial brain component, the three coils are located in a turn-off state. The water molecules in the rectangular volume spaces and the water molecules in the gel are in a normal magnetic resonance signal imaging state. During the task state scanning, the external power supply controller is turned on and turned off according to a set pulse frequency in cooperation with a scanning sequence so as to generate pulse current in the coils. The pulse current (the duration is not greater than 6 ms) changes the uniformity of a local magnetic field at the water molecules in the rectangular volume spaces to cause a T2* time change, and 1-3% of signal difference is generated with conventional scanning T2*. Alternate and continuous occurrence of the signal difference of the conventional scanning and task state scanning is realized, and the duration is not smaller than 6 min, therefore, a function of simulating the BOLD signals of the human brain is realized.

The external power supply controller includes a fiber receiver, a frequency-to-voltage converter, a current driver and a remote control coil. The external power supply controller can be programmed to achieve simultaneous and independent turn-on/turn-off ($\geq 200$/s), high and low current switching (1 mA or $\leq 0.5$ mA) and BOLD signal simulation of one or more functional areas of the coils in the three volume spaces; and sequential and independent turn-on/turn-off (the interval time$\leq 6$ ms) and high and low current switching of coils in the three volume spaces can also be realized for analyzing and simulating the brain connection of different functional areas.

The phantom is provided with image post processing software. The software can be installed on Windows series platforms and a Linux platform. The software is used for extracting brain contours of brain function magnetic resonance sequence images (.img/.dcm format) obtained by magnetic resonance systems of various manufacturers without changing the formats. That is, "scalp removal" operation in a function magnetic resonance image processing course, and meanwhile excitation sequence data of the external power supply controller are automatically imported into the conventional magnetic resonance imageprocessing software (SPM, AFNI, FSL, etc.). Although the specific embodiments of the present invention have been described above in combination with the drawings, it is not intended to limit the protection scope of the present invention, and those skilled in the art should understand that various modifications or variations, which may be made by those skilled in the art on the basis of the technical solutions of the present invention without any creative effort, shall still fall within the protection scope of the present invention.

The invention claimed is:

1. A functional magnetic resonance imaging quality detection phantom, comprising two independent shells which are movably connected with each other, wherein a BOLD simulation signal module is arranged in the first shell, and a basic imaging detection module is arranged in the second shell;
   the BOLD simulation signal module comprises a locating accuracy test component and a BOLD signal simulation component, wherein the locating accuracy test component comprises two locating blocks placed in a crossing manner, a wedge-shaped passage composed of isosceles right triangle blocks is arranged on the locating blocks, and the BOLD signal simulation component comprises an artificial brain for functional magnetic resonance imaging; and
   the basic imaging detection module comprises a locating accuracy test component, a geometric distortion test component, a high contrast component and a layer deviation measurement component, which are independent from each other, and the geometric distortion test component is of a multilayer grid structure to simulate the geometric distortion degrees of images of various directions; the high contrast component comprises a substrate and multiple rows of through holes with different apertures formed in the substrate; and the layer deviation measurement component comprises a basement layer and two orthogonal gaps formed on the basement layer.

2. The functional magnetic resonance imaging quality detection phantom of claim 1, wherein both the first shell and the second shell are cylindrical shells made of organic glass, the two shells have the same diameter, and the height of the first shell is larger than that of the second shell.

3. The functional magnetic resonance imaging quality detection phantom of claim 1, wherein bayonets are formed in the outer sides of both the first shell and the second shell, and the two shells are connected together through the bayonets.

4. The functional magnetic resonance imaging quality detection phantom of claim 1, wherein:
   the geometric distortion test component comprises multiple layers of grids, the aperture of the check of each grid is the same, and the thicknesses of the sides of the checks are the same, the distance between the vertexes of two arbitrary checks is measured on the obtained image by scanning each layer, the distance is compared with the real distance to obtain the geometric distortion degree of the image on the axial direction, and the distances between the vertexes of the checks of different layers are measured to obtain the geometric distortion on a sagittal direction and a coronal direction.

5. The functional magnetic resonance imaging quality detection phantom of claim 4, wherein the grids are made of a PVC material, and three layers of grids are arranged.

6. The functional magnetic resonance imaging quality detection phantom of claim 1, wherein multiple rows of through holes with different diameters are formed in the substrate of the high contrast component, multiple through holes are formed in each row, the diameters of the through holes on the same row are the same, the intervals between the through holes having the same diameters are equal to their diameters, through hole images are observed on the obtained image by scanning, and if the holes having the same diameters are clear and the signals are not connected with each other, the minimum aperture satisfying the condition is a limit visual width.

7. The functional magnetic resonance imaging quality detection phantom of claim 1, wherein the wedge shapes on the locating blocks of the locating accuracy test component are arranged in a crossing manner, a locating line is arranged at the intersection of long sides of the two locating blocks, if the lengths of black long dark strips formed in the scanned image are equal, it indicates that the locating is accurate, otherwise, there is a locating deviation.

8. The functional magnetic resonance imaging quality detection phantom of claim 1, wherein gaps of a 45-degree angle are formed on the basement layer of the layer deviation measurement component, the two gaps are orthogonal, the widths of the gaps are the same, and an actual layer thickness is calculated and confirmed through a signal formed by the two gaps on the scanned image to obtain a setting layer thickness deviation.

9. The functional magnetic resonance imaging quality detection phantom of claim 1, wherein a setting area in the second shell is scanned to obtain the signal, noise and variance value of the area, and the signal to noise ratio of the image is calculated.

10. The functional magnetic resonance imaging quality detection phantom of claim 1, wherein the artificial brain in the shape of the BOLD signal simulation component is made of hydrogel containing 0.5-1% of copper sulfate, 0.3-0.5% of sodium chloride, 1-1.25% of agarose, 0.100-0.125% of Gd-DTPA and is used for simulating $T_1$ and $T_2$ relaxation values of a gray matter of a human brain under magnetic resonance.

11. The functional magnetic resonance imaging quality detection phantom of claim 10, wherein the artificial brain has the structure shape of a human brain, an opisthencephalon, a ventricle and a gyms.

12. The functional magnetic resonance imaging quality detection phantom of claim 1, wherein a hollow cavity is respectively arranged on a frontal lobe position and a sea horse position of the artificial brain corresponding to the transverse short axis direction of the first shell, a hollow cavity is arranged at a gyms cinguli position of the artificial brain corresponding to the longitudinal long axial line direction of the first shell, and a coil is arranged in each hollow cavity.

13. The functional magnetic resonance imaging quality detection phantom of claim 12, wherein the coil extends out from the first shell along the longitudinal axial line direction of the first shell and is connected with an external power supply controller through a connecting line.

14. The functional magnetic resonance imaging quality detection phantom of claim 1, wherein the external power supply controller is a programmable controller, and controls the turn-on, duration or turn-off between power supply and the coils and meanwhile controls the on/off time, duration and frequency.

* * * * *